United States Patent [19]

Hoffmann et al.

[11] 4,140,734
[45] Feb. 20, 1979

[54] ALKOXYETHYL DITHIOPHOSPHONIC ACID ESTER HALIDES

[75] Inventors: Hellmut Hoffmann, Wuppertal, Fed. Rep. of Germany; Junichi Saito, Tokyo, Japan

[73] Assignee: Bayer Aktiengesellschaft, Leverkusen, Fed. Rep. of Germany

[21] Appl. No.: 848,416

[22] Filed: Nov. 3, 1977

[30] Foreign Application Priority Data

Nov. 20, 1976 [DE] Fed. Rep. of Germany ....... 2652922

[51] Int. Cl.² .............................................. C07F 9/42
[52] U.S. Cl. .................................. 260/950; 260/972; 260/985
[58] Field of Search ......................................... 260/950

[56] References Cited

U.S. PATENT DOCUMENTS 3,733,379   5/1973   Szabo .................................. 260/950

Primary Examiner—Anton H. Sutto
Attorney, Agent, or Firm—Sprung, Felfe, Horn, Lynch & Kramer

[57] ABSTRACT

Alkoxyethyl dithiophosphonic acid ester halide intermediates of the formula

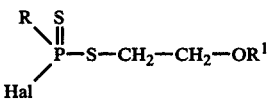

in which
R is alkyl or phenyl,
R¹ is alkyl, and
Hal is halogen are prepared by reacting an alkane- or phenylphosphine dihalide of the formula

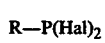

with an alkoxyethylsulphenyl chloride of the formula

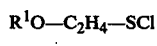

and thereafter with at least the stoichiometric amount of hydrogen sulphide. The sulphenyl chloride is produced by reacting sodium disulphide with the appropriate 2-alkoxy-alkyl halide and then with sulphuryl chloride. The novel compounds can be esterified with phenols to produce insecticides.

5 Claims, No Drawings

ALKOXYETHYL DITHIOPHOSPHONIC ACID ESTER HALIDES

The present invention relates to certain new dithiophosphonic acid ester halides, to an unobvious process for their preparation and to their use as intermediates for the synthesis of O-arylalkanedithiophosphonic acid esters that are suitable as pesticides.

The following processes for the preparation of O-arylalkanedithiophosphonic acid esters, for example O-[2,4-dichlorophenyl]-S-(2-ethoxy-ethyl)-methanedithiophosphonic acid ester, are already known:

Reaction of alkanethionophosphonic acid dihalides with phenolates, which may or may not be nuclear-substituted, to give the corresponding O-phenyl-alkanethionophosphonic acid ester monohalides, followed by either (a) treatment with hydrogen sulphide and alkali metal carbonates, preferably potassium carbonate, to form alkali metal O-phenyl-alkanedithiophosphonates, and subsequent reaction with the appropriate 2-alkoxyethyl halides, or (b) reaction of the O-phenyl-alkane-thionophosphonic acid ester monohalide formed, with 2-alkoxy-ethylmercaptans.

Considerable difficulties are encountered, when carrying out process variant (a), in respect of the purification of the alkali metal salt of the O-phenyl-alkanedithiophosphonate. Furthermore, the reaction with the 2-alkoxyethyl halide takes place very slowly and incompletely; it therefore gives the desired end product in poor yields only.

In process variant (b), the O-phenyl-alkanethionophosphonic acid ester halide formed as an intermediate is obtainable in insufficient purity only. Furthermore, the reaction must be carried out with an excess of hydrogen sulphide, causing problems concerned with waste air and waste water.

The present invention provides, as new compounds, the dithiophosphonic acid ester halides of the general formula

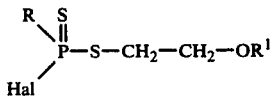
 (I), in which
R denotes alkyl or phenyl,
R¹ denotes alkyl and
Hal denotes halogen.

The compounds of the formula (I) are valuable intermediates which are, in particular, suitable for the preparation of dithiophosphonic acid esters which can be used as highly effective pesticides.

Preferably, R denotes phenyl or straight-chain or branched alkyl with 1 to 6 (especially 1 to 3) carbon atoms, R¹ denotes straight-chain or branched alkyl with 1 to 4 carbon atoms (especially ethyl) and Hal denotes chlorine.

The invention also provides a process for the preparation of a dithiophosphonic acid ester halide (I) in which an alkane- or phenyl-phosphine dihalide of the general formula R—P(Hal)₂ (II)

in which

R has the above-mentioned meaning and
Hal represents halogen, preferably chlorine, is reacted first with an alkoxyethylsulphenyl chloride of the general formula R¹O—C₂H₄—SCl (III), in which R¹ has the above-mentioned meaning,
if appropriate in the presence of a solvent and, if appropriate, in a nitrogen atmosphere, and subsequently with at least the stoichiometric amount of hydrogen sulphide.

Surprisingly, the compounds (I) can be obtained, by the process according to the invention, in high purity and with good yields. They can be directly reacted further, without intermediate isolation or purification. The compounds according to the invention represent an enrichment of the art.

If, for example, methanedichlorophosphine, 2-ethoxyethylsulphenyl chloride and hydrogen sulphide are used as starting materials, the course of the reaction can be represented by the following equation:

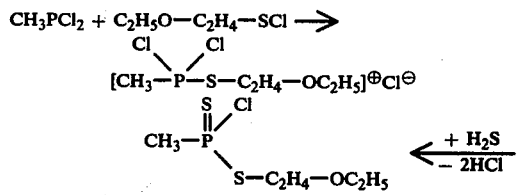

The phosphine dihalides of the formula (II) are known from the literature and can easily be prepared in accordance with customary processes (see, for example, Netherlands published Patent Application No. 6,806,504; SU Patent Specifications Nos. 159,527, 160,184 and 196,818).

The following may be mentioned as examples of the phosphine dihalides (II): methane-, propane- and phenylphosphine dichloride.

The 2-alkoxy-ethylsulphenyl halides (III) can be prepared in accordance with processes which are known in principle [see Chem. Reviews 39, pages 269–332 (1946)], for example by reacting 2-alkoxyethyl chlorides with sodium disulphide and then with sulphuryl chloride, if appropriate in the presence of a solvent, in accordance with the following equation:

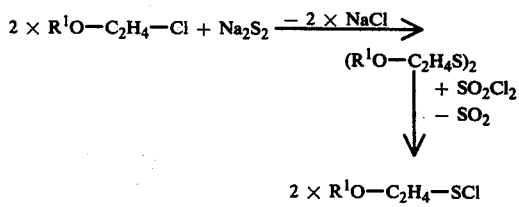

in which R¹ has the above-mentioned meaning. in which

The following may be mentioned as examples of the 2-alkoxyethylsulphenyl chlorides (III): methoxy-, ethoxy- or propoxy-ethylsulphenyl chloride.

The process for the preparation of the compounds according to the invention is preferably carried out in the presence of a suitable solvent or diluent. Virtually all inert organic solvents can be used for this purpose, especially aliphatic and aromatic, optionally chlorinated hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

The reaction temperature can be varied within a substantial range. In general, the reaction is carried out at from −30° to 110° C., preferably at from −30° to 100° C.

In general, the reaction is allowed to take place under normal pressure.

To carry out the process, the starting components are in most cases employed in equimolar amounts. Preferably, the phosphine dihalide (II), dissolved in one of the abovementioned organic solvents, is initially introduced at a low temperature and the sulphenyl chloride (III) is added dropwise under an inert, usually a nitrogen, atmosphere. The end of the reaction manifests itself in a change of color of the reaction mixture from white to yellow. After 30 minutes, hydrogen sulphide is passed into the suspension, in the course of which the temperature of the mixture rises. The batch is worked up by concentrating the reaction mixture under reduced pressure.

As already mentioned, the compounds according to the invention represent intermediates, obtainable easily and in good yields, for the synthesis of O-aryl-alkanedithiophosphonic acid esters suitable as pesticides:

The 2-alkoxy-ethylsulphenyl halides required as starting materials could be prepared, for example, as follows:

EXAMPLE 1a: $(C_2H_5O-CH_2-CH_2-S)_2$ 58 g of sodium sulphide containing 9 moles of water of crystallization were melted and 6.4 g of pulverulent sulphur were dissolved in the molten salt. After a deep red, clear solution had formed, the solution was cooled to 50° C. and 30 ml of dimethylformamide were added. 43.2 g of 2-ethoxyethyl chloride were then added dropwise to the reaction mixture at a temperature of 57–60° C. After completion of the addition, the batch was stirred at the stated temperature for one hour and was then poured into cold water and the reaction product was extracted with toluene, concentrated and distilled. The yield was 34.1 g (81% of theory) of bis-(2-ethoxyethyl) disulphide, of boiling point 87–100° C./1 mm Hg.

1b: $C_2H_5O-CH_2-CH_2-SCl$ (A) From distilled bis-(2-ethoxyethyl) disulphide 42 g of bis-(2-ethoxyethyl) disulphide were dissolved in 50 ml of carbon tetrachloride and 30 g of sulphuryl chloride were added dropwise at a temperature of 0–3° C. The reaction mixture was then stirred for 1 hour at room temperature, after which it was distilled. The yield was 53.3 g (95% of theory) of 2-ethoxyethylsulphenyl chloride of boiling point 53° C./14 mm Hg.

(B) From non-distilled bis-(2-ethoxyethyl) disulphide (water as the solvent)

48 g of sodium sulphide containing 9 moles of water of crystallization were dissolved in 50 ml of hot water and 6.4 g of pulverulent sulphur were added in order to dissolve. After a deep red, clear solution had formed, 43.2 g of 2-ethoxyethyl chloride were added to the reaction mixture at 90–100° C., the mixture was then cooled and extracted with toluene, and the extract was dried and concentrated. 10 ml of carbon tetrachloride were than added to the crude product, and the latter was chlorinated dropwise by adding 30 g of sulphuryl chloride at a temperature below 3° C. The mixture was then stirred vigorously for 1 hour. Fractional distillation gave 35.8 g (64% of theory) of 2-ethoxyethylsulphenyl chloride.

(C) Dimethylformamide as the solvent

The bis-(2-ethoxy-ethyl) disulphide was prepared as in Example 1a and was then chlorinated as described under (B), but without fractional distillation of the bis-(2-ethoxyethyl) disulphide. The yield was 43 g (77% of theory).

The starting materials are converted to the novel compounds by the preparative examples which follow:

EXAMPLE 2

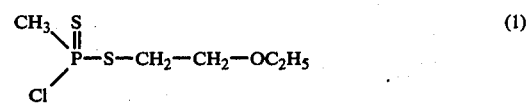

31.7 g (0.225 mol) of 2-ethoxyethylsulphenyl chloride were added, under a nitrogen atmosphere, to 25.5 g (0.22 mol) of methanedichlorophosphine, dissolved in 30 ml of carbon tetrachloride, the solution being cooled to a low temperature (below −30° C.). The reaction mixture became viscous and a white solid precipitated. The end point of the reaction was detectable by a change in color of the mixture from white to light yellow. After stirring for 30 minutes, hydrogen sulphide was blown into the suspension, until a clear solution was obtained, in the course of which the internal temperature rose from −10° C. to 0–10° C., and the batch was then concentrated under reduced pressure. 46.1 g (97% of theory) of S-(2-ethoxyethyl) -methanedithiophosphonic acid ester chloride were obtained in 90–95% purity.

The following compound could be prepared analogously:

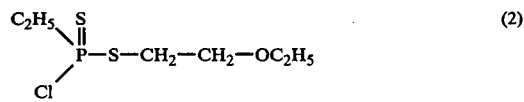

The corresponding phenyl derivative, of the formula shown below, could also be prepared analogously, though at temperatures between 80° and 100° C.:

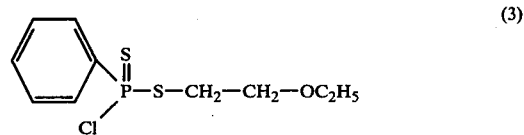

EXAMPLE 3

The conversion of the compounds (I) of the invention by reaction with optionally nuclear-substituted phenols or thiophenols to give the O-aryl-alkane-dithiophosphonic acid esters which can be used as highly active pesticides is illustrated by the following experiment.

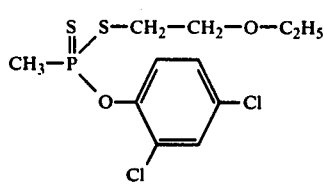

A solution of 81.5 g (0.5 mol) of 2,4-dichlorophenol, 22 g (0.55 mol) of sodium hydroxide and 55 ml of water was added dropwise over the course of 60 minutes to 95 g (0.5 mol) of S-(2-ethoxyethyl) -methanedithiophosphonic acid ester chloride at +5° C. to +10° C., and the reaction mixture was stirred for a further hour, at 15-20° C. Thereafter the reaction batch was poured into 150 ml of cold water and extracted with 150 ml of toluene. The toluene extract was freed from the solvent and concentrated under reduced pressure. 137 g (79.5% of theory) of O-(2,4-dichlorophenyl)- S-(2-ethoxyethyl)-methanedithiophosphonic acid ester were obtained in 92% purity.

The foregoing ester is a known insecticide, active for example against *Musca Domestica*. It can be applied to walls, air space, plants or animals in 100% strength or as a dilute emulsion in water, e.g. 0.01% by weight, optionally with appropriate emulsifying agents, or as a similar solution in a volitable organic solvent.

It will be appreciated that the instant specification and examples are set forth by way of illustration and not limitation, and that various modifications and changes may be made without departing from the spirit and scope of the present invention.

What is claimed is:

1. A dithiophosphonic acid ester halide of the formula

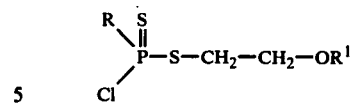

in which
R is alkyl or phenyl, and
$R^1$ is alkyl.

2. A compound according to claim 1, in which
R is phenyl or alkyl with 1 to 6 carbon atoms, and
$R^1$ is alkyl with 1 to 4 carbon atoms.

3. A compound according to claim 1, wherein such compound is S-(2-ethoxyethyl)-methanedithiophosphonic acid ester chloride of the formula

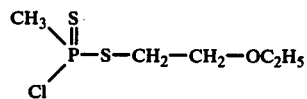

4. A compound according to claim 1, wherein such compound is S-(2-ethoxyethyl) -ethanedithiophosphonic acid ester chloride of the formula

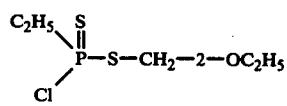

5. A compound according to claim 1, wherein such compound is S-(2-ethoxyethyl)-phenyldithiophosphonic acid ester chloride of the formula

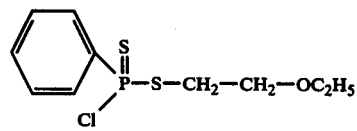

* * * * *